(12) United States Patent
Albers et al.

(10) Patent No.: US 8,308,658 B2
(45) Date of Patent: Nov. 13, 2012

(54) MEDICAL GUIDEWIRE

(75) Inventors: Jason M. Albers, Buffalo, MN (US);
Eugene Champeau, Medina, MN (US);
David Liebl, Eden Prairie, MN (US)

(73) Assignee: NeoMetrics, Inc., Plymouth, MN (US)

( * ) Notice: Subject to any disclaimer, the term of this patent is extended or adjusted under 35 U.S.C. 154(b) by 1184 days.

(21) Appl. No.: 11/735,289

(22) Filed: Apr. 13, 2007

(65) Prior Publication Data
US 2008/0255518 A1    Oct. 16, 2008

(51) Int. Cl.
*A61M 25/00*    (2006.01)
*A61M 25/09*    (2006.01)

(52) U.S. Cl. .................................. 600/585; 604/164.13
(58) Field of Classification Search .................. 600/585; 604/164

See application file for complete search history.

(56) References Cited

U.S. PATENT DOCUMENTS

| | | | |
|---|---|---|---|
| 3,789,841 A | 2/1974 | Antoshkiw | |
| 3,973,556 A * | 8/1976 | Fleischhacker et al. | 600/585 |
| 4,724,846 A | 2/1988 | Evans, III | |
| 4,798,598 A * | 1/1989 | Bonello et al. | 604/528 |
| 4,811,743 A | 3/1989 | Stevens | |
| 4,832,047 A | 5/1989 | Sepetka et al. | |
| 4,867,173 A | 9/1989 | Leoni | |
| 4,921,482 A * | 5/1990 | Hammerslag et al. | 604/95.01 |
| 4,925,445 A | 5/1990 | Sakamoto et al. | |
| 4,940,062 A * | 7/1990 | Hampton et al. | 600/585 |
| 4,971,490 A | 11/1990 | Hawkins | |
| 4,984,581 A | 1/1991 | Stice | |
| 4,998,916 A * | 3/1991 | Hammerslag et al. | 604/528 |
| RE33,911 E | 5/1992 | Samson et al. | |
| 5,176,149 A | 1/1993 | Grenouillet | |
| 5,234,003 A | 8/1993 | Hall | |
| 5,238,004 A | 8/1993 | Sahatjian et al. | |
| 5,259,393 A | 11/1993 | Corso, Jr. et al. | |
| 5,409,015 A | 4/1995 | Palermo | |
| 5,477,864 A | 12/1995 | Davidson | |
| 5,480,382 A | 1/1996 | Hammerslag et al. | |
| 5,488,959 A | 2/1996 | Ales | |
| 5,522,875 A | 6/1996 | Gates et al. | |
| 5,606,981 A | 3/1997 | Tartacower et al. | |
| 5,636,641 A | 6/1997 | Fariabi | |
| 5,636,642 A | 6/1997 | Palermo | |
| 5,664,580 A | 9/1997 | Erickson et al. | |
| 5,673,707 A | 10/1997 | Chandrasekaran | |
| 5,682,894 A | 11/1997 | Orr et al. | |
| 5,706,826 A * | 1/1998 | Schwager | 600/585 |
| 5,720,300 A | 2/1998 | Fagan et al. | |
| 5,769,796 A | 6/1998 | Palermo et al. | |
| 5,797,856 A * | 8/1998 | Frisbie et al. | 600/585 |
| 5,807,279 A | 9/1998 | Viera | |
| 5,830,155 A * | 11/1998 | Frechette et al. | 600/585 |
| 5,865,767 A * | 2/1999 | Frechette et al. | 600/585 |
| 5,865,768 A | 2/1999 | Orr | |
| 5,891,055 A | 4/1999 | Sauter | |
| 5,891,056 A * | 4/1999 | Ramzipoor | 600/585 |
| 5,916,166 A | 6/1999 | Reiss et al. | |
| 5,938,623 A | 8/1999 | Quiachon et al. | |

(Continued)

*Primary Examiner* — Sean Dougherty
(74) *Attorney, Agent, or Firm* — Fredrikson & Byron, P.A.

(57) ABSTRACT

The guidewire provides a core and wire coil construction. The core can be shaped with a generally squared-off distally facing shoulder that forms a platform for a proximal end portion of the wire coil. The wire coil can have a plurality of spaced apart coil turns at its proximal end portion. A bonding agent comprising an adhesive can be used to secure the core to the wire coil proximal end portion.

34 Claims, 4 Drawing Sheets

U.S. PATENT DOCUMENTS

| | | | |
|---|---|---|---|
| 5,954,672 A * | 9/1999 | Schwager | 600/585 |
| 6,113,557 A | 9/2000 | Fagan et al. | |
| 6,183,420 B1 | 2/2001 | Douk et al. | |
| 6,203,485 B1 | 3/2001 | Urick | |
| 6,254,549 B1 * | 7/2001 | Ramzipoor | 600/585 |
| 6,325,766 B1 | 12/2001 | Anderson et al. | |
| 6,336,906 B1 | 1/2002 | Hammarstrom et al. | |
| 6,390,992 B1 * | 5/2002 | Morris et al. | 600/585 |
| 6,409,683 B1 | 6/2002 | Fonseca et al. | |
| 6,482,166 B1 | 11/2002 | Fariabi | |
| 6,673,025 B1 * | 1/2004 | Richardson et al. | 600/585 |
| 6,832,715 B2 | 12/2004 | Eungard et al. | |
| 7,494,474 B2 * | 2/2009 | Richardson et al. | 600/585 |
| 7,641,622 B2 * | 1/2010 | Satou et al. | 600/585 |
| 2004/0092845 A1 * | 5/2004 | Gaber | 600/585 |
| 2004/0167436 A1 | 8/2004 | Reynolds et al. | |
| 2004/0181174 A2 * | 9/2004 | Davis et al. | 600/585 |
| 2005/0038359 A1 | 2/2005 | Aimi et al. | |
| 2005/0049523 A1 | 3/2005 | Crank | |
| 2005/0054952 A1 | 3/2005 | Eskuri et al. | |
| 2006/0047224 A1 | 3/2006 | Grandfield | |
| 2006/0089568 A1 | 4/2006 | Nuss | |
| 2008/0161726 A1 * | 7/2008 | Itou | 600/585 |
| 2008/0194992 A1 * | 8/2008 | Satou et al. | 600/585 |

* cited by examiner

MEDICAL GUIDEWIRE

BACKGROUND

1. Field of the Invention

The present invention relates to the field of medical devices and more particularly to guidewires for use primarily in intravascular procedures.

2. Description of the Related Prior Art

A major requirement for medical guidewires and other guiding members, whether they are formed of solid wire or tubular members, is that they have sufficient column strength and stiffness to be pushed through passageways in a patient, such as the patient's vascular system, with minimal kinking or binding. However, the distal section of the guidewire must also be flexible enough to avoid damaging the blood vessel or other body lumen through which it is advanced. Accordingly, efforts have been made to provide guidewires having a favorable combination of both strength and flexibility in order to make them suitable for their intended uses. However, strength for pushing and flexibility for turning without damaging vascular walls tend to be diametrically opposed to one another, such that an increase in one usually involves a decrease in the other, as exemplified below.

The cores of conventional guidewires have been made of many different materials. Two of the more popular materials are stainless steel and Nitinol. In particular, stainless steel has good pushability properties as well as good torque qualities. In turn, guidewire cores formed of such material are generally found suitable for being advanced, and further, for being rotated, so as aid in their being maneuvered, through a patient's vascular system. However, such steel core guidewires tend to be stiff, i.e., not easily bent, and limited in their flexibility. As such, if the steel guidewire is not carefully used, the potential exists for damaging the vessel/body lumen through which it is being advanced. In addition, the steel can be found to bind or kink when rotated since it does not readily flex. As is known, once the guidewire is kinked, it must often be discarded and replaced with a new guidewire.

On the other hand, guidewires formed with Nitinol cores are found to have the flexibility that is warranted for negotiation through a tortuous path in a patient's body lumens or vessels. In turn, when being advanced through a patient's vascular system, such guidewires are found to exhibit lower potential for either damaging the patient's vessel/body lumen or kinking/binding. Unfortunately, such Nitinol guidewires are found to be too soft. As such, they cannot be torqued as readily as stainless steel, thereby limiting their maneuverability. In addition, Nitinol guidewires tend to have good shape memory. Accordingly, they are found to have limited pushability against resistance of tortuosity (e.g., in comparison to guidewires having stainless steel cores) because they tend to straighten out or return to their original shape during their advancement. The shape memory can make it difficult for a physician to shape the tip of the guidewire with his fingers for accessing difficult to reach portions of the patient's vascular system.

As is known, there has been a gradual decrease in the diameter profiles or transverse dimensions of commercially available guidewires, particularly for their use in coronary arteries. Accordingly, these guidewires can be more universally applied in a wide variety of medical procedures. For example, when materials generally known to be rigid or stiff are formed to have decreased profiles, such materials (and the guidewires that they are used in forming) can be found to exhibit greater flexibility. However, associated with the decrease in profile has also been a general loss in pushability.

In light of the above, many conventional guidewires now utilize a wire coil or spring positioned around a distal end section of the guidewire core. In such guidewires, except for the end of the core (which is typically expanded in size), the rest of the distal end section is generally tapered so as to accommodate the coil. In combining the use of such wire coil with a tapered and thinner core for the distal end section, strength as well as flexibility can be achieved in the guidewire. In particular, longitudinal strength along the guidewire distal section is provided via the addition of the wire coil, while lateral flexibility across the guidewire distal section is provided via the tapered core section as well as the inherent lateral flexibility of the wire coil. Unfortunately, there have been a number of limitations found with this design.

In some cases, proximal and distal ends of the wire coil are respectively secured to proximal and distal ends of the distal end section of the core; however, in other cases, none or only one of the wire coil ends are secured to the core. In cases where one or both of the wire coil ends are secured, welding is often used. Welding is advantageous because it involves a relatively easy and inexpensive securing process and effectively provides a rigid point/section of connection for the bodies (i.e., the core and wire coil) being affixed together. Accordingly, when welding is used in securing the wire coil ends to the core, the resulting welds tend to enhance the overall pushability properties of the guidewire at its distal section (via the securement of the wire coil to the core), while still enabling the guidewire's distal section to be flexible (via the tapered core section and the wire coil) so as to be negotiated through a patient's body lumens or vessels. However, because the welds form such a rigid connection, the flexibility of the guidewire, particularly at the welds, is limited. Further, because the welds are rigid, they are generally stressed during repeated bending of the guidewire during its maneuvering. In particular, the welds at the proximal end of the wire coil are generally found to be more stressed than the welds at the distal end of the wire coil because the guidewire often bends at higher degrees along its length than at its end. In turn, such proximally located welds can be found to break after repeated use.

Conversely, in cases where the wire coil ends are not secured to the core, the pushability properties of the guidewire are accordingly found to be limited. In addition, the tapered and thinner (and thereby, softer) core section can be found to not properly engage the wire coil. As such, when rotating the guidewire, there often is not a proper transfer of torque between the core and the wire coil. In turn, the guidewire's maneuverability is also found to be limited. Consequently, the wire coil can be found to kink when being advanced around bends, e.g., in a patient's vascular system.

What are needed are apparatus and systematic methods to address or overcome one or more of the limitations briefly described above with respect to conventional guidewires.

SUMMARY OF THE INVENTION

Embodiments of the invention provide a guidewire that exhibits an innovative blend of favorable properties, including enhanced flexibility and enhanced pushability, as opposed to other commercially available guidewires. The guidewire provides a core and wire coil construction.

In one embodiment, the wire coil has spaced apart coil turns at a proximal end portion thereof, with the spaced apart coil turns forming gaps there between. A bonding agent comprising an adhesive joins the core to the proximal end portion of the wire coil. The bonding agent fills one or more of the gaps between the spaced apart coil turns at the proximal end portion of the wire coil, thereby providing a significant junction area between the core and the wire coil as well as flexibility at the junction area during advancement of the guidewire through a patient's body lumens or vessels.

In another embodiment, the core has a generally squared-off distally facing shoulder provided uniformly around the core. A proximal end portion of the wire coil is seated at least proximate to the distally facing shoulder with the distally facing shoulder forming a platform for the wire coil proximal end portion. A bonding agent comprising an adhesive joins the proximal end portion of the wire coil at the distally facing shoulder. The proximal end portion of the wire coil is stabilized when seated at least proximate to the distally facing shoulder and joined to the core at the distally facing shoulder, thereby providing pushability at a distal section of the core during advancement of the guidewire through a patient's body lumens or vessels as well as flexibility at junction area between the core and the wire coil during advancement of the guidewire through a patient's body lumens or vessels.

In a further embodiment, the core has a generally squared-off distally facing shoulder provided uniformly around the core. The wire coil has spaced apart coil turns at a proximal end portion thereof, with the spaced apart coil turns forming gaps there between. The proximal end portion of the wire coil is seated at least proximate to the distally facing shoulder with the distally facing shoulder forming a platform for the wire coil proximal end portion. A bonding agent comprising an adhesive joins the core to the proximal end portion of the wire coil. The bonding agent fills one or more of the gaps between the spaced apart coil turns at the proximal end portion of the wire coil, thereby providing a significant junction area between the core and the wire coil as well as flexibility at the junction area during advancement of the guidewire through a patient's body lumens or vessels. The proximal end portion of the wire coil is stabilized when seated at least proximate to the distally facing shoulder and joined to the core at the distally facing shoulder, thereby providing pushability at a distal section of the core during the advancement of the guidewire.

DETAILED DESCRIPTION

Figure 1:
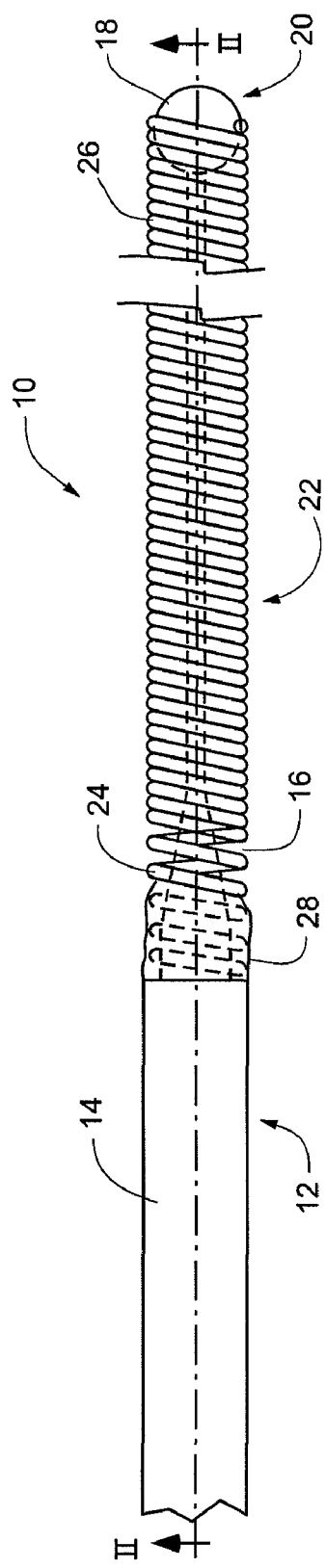
FIG. 1 is a side view of the guidewire in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Guidewires are employed in a wide variety of medical procedures. As is known, guidewires are typically used to facilitate the placement of medical devices inside a patient's body. For example, one well-known procedure involves using guidewires for inserting catheters and other devices in the vascular system of the patient. As should be appreciated, the guidewires embodied herein should not be limited with respect to their scope of use. Instead, the embodied guidewires of the invention are applicable to any medical procedure in which a guidewire can or may be used.

As described above, a primary consideration in designing guidewires involves determining how best to achieve a sufficient combination of column strength and distal end flexibility. As further described above, a variety of efforts have been put forth to achieve such a combination; however, such efforts have generally resulted in limited success. For example, locating a guidewire core material that exhibits such a combination of properties has been difficult. Similarly, decreasing the core profile of the guidewire to achieve this combination has generally been unsuccessful. One approach that has resulted in some success involves using a wire coil at the distal end of the guidewire. However, limitations have also been encountered with this design, as described above.

Embodiments of the invention provide guidewires having constructions which overcome one or more of the above-described limitations of conventional guidewires. In particular, the guidewires embodied herein provide an innovative blend of favorable properties, including enhanced pushability and/or enhanced flexibility, as well as having other construction characteristics and/or properties which make them advantageous over commercially available guidewires.

FIG. 1 illustrates a guidewire used in accordance with certain embodiments of the invention. As shown, the guidewire 10 has three main elements. One of these elements is an elongated, solid core 12. In certain embodiments, such core 12 has a generally round cross section; however, the invention should not be limited to such. For example, while not shown, the core 12, instead of having a round cross-section, can have one or more flat outer surfaces. As should be appreciated, the core 12 can be any desirable length, and is accordingly sized based on the procedure(s) in which the guidewire 10 is intended. For example, in certain embodiments, the core 12 can be sized to be greater than about one meter in length in order to be advanced through a corresponding length of a patient's body lumens or vessels (not shown), e.g., in the patient's vascular system.

As illustrated, the core 12 includes a proximal section 14 having a generally uniform diameter and a distal section 16 (mostly covered in FIG. 1, but shown with dashed lines where covered) having a generally varying diameter. In certain embodiments, the distal section 16 includes an expanded portion 18 at its distal end 20. In certain embodiments, the distal end 20 is initially shaped to be compact (e.g., resembling a rectangular block or any other desirable shape) and then modified (as later described herein) to form the expanded portion 18. The core 12 can be generally made of any metal, as further described below. In certain embodiments, the metal of the core 12 can include any single metal or combination of metals. Additionally, in certain embodiments, if the core 12 includes a combination of metals, the metals can be provided together in a mixture or alternatively, be provided separately and then adjoined (e.g., one metal forming the proximal section 14 joined to another metal forming the distal section 16).

Another element of the guidewire 10 is a wire coil 22, which is received about the tapered distal section 16 of the core 12. In certain embodiments, the wire coil 22 can be made of tungsten, platinum, stainless steel, palladium, and the like; however, embodiments of the invention should not be limited to such. Instead, the wire coil 22 can be made of any single metal or combination of metals formed together or joined in any desirable fashion, similar to that described above with respect to the core 12. One material that may be selected for its radiopaque nature and low cost is tungsten. In certain embodiments, as shown, the wire coil 22, at its proximal end portion 24, has coil turns that are spaced apart from one another, while at its distal end portion 26, adjacent coil turns are in contact with each other. These features of the wire coil 22, in certain embodiments, have been found to contribute to innovative functioning of the guidewire 10, as further described below.

The wire coil 22 is generally flexible and has a proximal end portion 24 and a distal end portion 26. In certain embodiments, as shown, the outer diameter of the wire coil 22 at its proximal end portion 24 is substantially similar to the diameter of the core 12 at its proximal section 14. As such, by stating that the outer diameter of the wire coil 22 is substantially similar to the diameter of the core 12 at its proximal section 14, the outer diameter of the wire coil 22 may be slightly larger or smaller than the diameter of the core 12 at its proximal section 14. As further shown, in certain embodiments, the wire coil 22 can have a generally uniform outer diameter over its length; however, the invention should not be limited to such. For example, in certain embodiments, the wire coil 22 may have an outer diameter that generally tapers from its proximal end portion 24 to its distal end portion 26. In turn, the wire coil 22 with tapered outer diameter, when slid over the tapered distal section 16 of the core 12, creates a more compact construction with the core 12. In certain embodiments, as described below, when the wire coil 22 has a tapered outer diameter, space remains between a portion of the core 12 and the wire coil 22 so as to enhance the flexibility of the wire coil 22 as the guidewire 10 is advanced through body lumens or vessels.

A further element of the guidewire 10 is a bonding agent 28, used to adhere at least a portion of the proximal end portion 24 of the wire coil 22 to the core 12. In certain embodiments, the bonding agent 28 is an adhesive. As should be appreciated, most adhesives are useful for bonding and exhibit greater flexibility then rigid bonding agents, even after the adhesives are cured. For example, one such adhesive can be an organic adhesive. Use of such a bonding agent 28, in certain embodiments, has been found to contribute to innovative functioning of the guidewire 10, as further described below. In certain embodiments, the bonding agent 28 is an adhesive which is curable via UV light. An exemplary adhesive can be a urethane adhesive, having methacrylate and acrylate oligomers and a photo initiator. As is known, such an adhesive is widely available from any of a number of commercial outlets.

Figure 2:
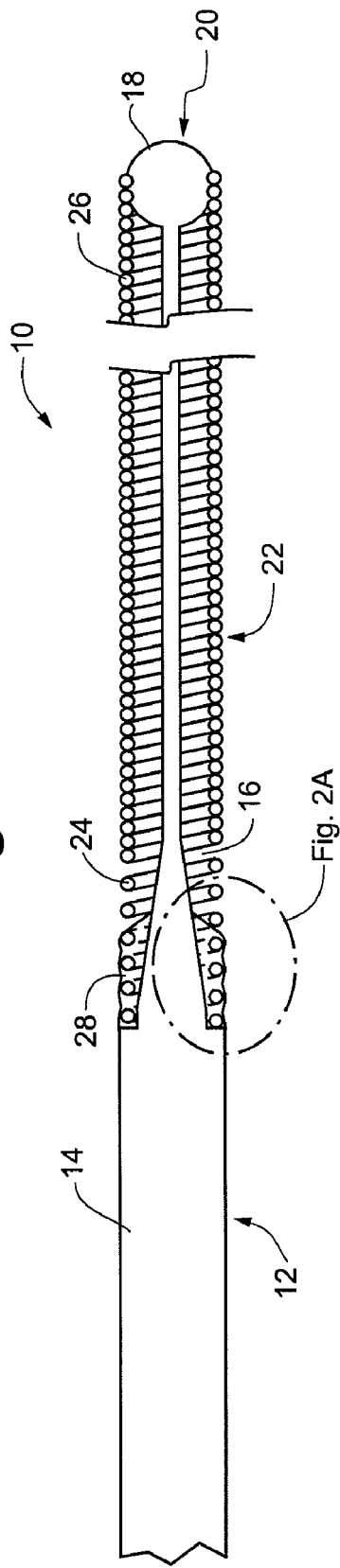
FIG. 2 is a cross-sectional view of the guidewire of FIG. 1 along the lines II-II.
Figure 2A:
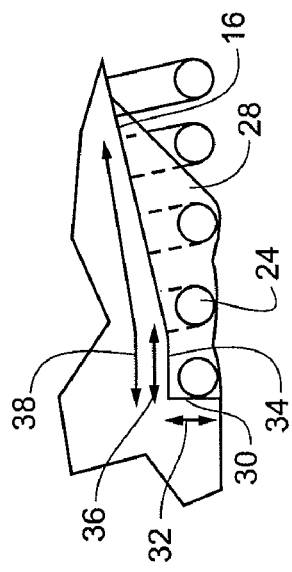
FIG. 2A is an enlarged view of a portion of the guidewire of FIG. 2.

In certain embodiments, when manufacturing the guidewire 10, the core 12 can be shaped using a centerless grinding technique, as well known by those skilled in the art. FIG. 2 shows a cross-section of the guidewire of FIG. 1 and FIG. 2A further shows an enlarged portion of FIG. 2, illustrating a portion of the advantageously shaped core 12. As illustrated in FIG. 2A, the core 12, in certain embodiments, can be shaped to have a distally facing shoulder 30. The distally facing shoulder 30, in certain embodiments, is generally squared-off on one or more of its inner and outer edges. As should be appreciated, in cases where the term "generally" is used herein, what is meant is "approximately". For example, "generally squared-off" can include squared-off (forming a 90° angle with one or more adjoining surfaces) as well as approximately squared-off (forming nearly a 90° angle with one or more adjoining surfaces). The distally facing shoulder 30 extends axially inward for a distance 32. In certain embodiments, the distance 32 is substantially similar in length to the diameter of a coil turn of the wire coil 22. As described above, the outer diameter of the wire coil 22 may be either slightly larger or slightly smaller than the diameter of the core 12 at its proximal section 14. Accordingly, the distance 32 can be slightly larger or smaller than the diameter of the coil turns of the wire coil 22, as warranted, e.g., with the distance 32 being a length of at least 75% of a diameter of a coil turn of the wire coil 22.

As shown, the shoulder 30 is uniformly provided around the core 12. Just distal of the shoulder 30 is a cylindrical portion 34 of the core 12. As illustrated, the cylindrical portion 34 extends distally from the shoulder 30 for a length 36. In certain embodiments, the length 36 is at least the same size as the diameter of at least one coil turn of the wire coil 22. In certain embodiments, as described above, the shoulder 30 is generally squared-off from the cylindrical portion 34 of the core 12; however, the invention should not be limited to such. Instead, while not shown, the shoulder 30, in certain embodiments, can have a tapering diameter as well (e.g., where the diameter of the core 12 decreases from the core proximal section 14 to the core cylindrical portion 34). However, in such cases, the taper of the shoulder 30 would be more squared-off than not (e.g., closer to forming a 90° angle with the cylindrical portion 34 than a 180° angle with the cylindrical portion 34). As such, whether the shoulder 30 is generally squared-off or tapered, the core 12 provides a platform via the shoulder 30 and cylindrical portion 34. However, as should be appreciated, if generally squared-off, as described above, the shoulder 30 provides a more effective platform for the proximal end portion 24 of the wire coil 22 as opposed to if the shoulder 30 is tapered between the core proximal section 14 and the core cylindrical portion 34.

By combining certain of the features described above and illustrated in FIGS. 1, 2, and 2A, the guidewire 10 provides enhanced functioning over conventional guidewire designs. For example, one such feature involves the spaced apart turns at the proximal end portion 24 of the wire coil 22. In certain embodiments, the spaced apart turns are spaced no further apart than the diameter of one coil turn. One purpose in configuring the wire coil 22 as such is to provide a significant bond between the wire coil 22 and the core 12 when using the bonding agent 28. As further described below, the bonding agent 28 fills gaps between the spaced apart turns, thereby providing this significant bond. When provided as an adhesive, the bonding agent 28 provides flexibility between the wire coil 22 and core 12 in this junction area during advancement of the guidewire 10 through a patient's body. For example, the junction of the wire coil 22 to the core 12 in this area would be less susceptible to stress-related breakdown during advancement and/or maneuvering of the guidewire 10 (as opposed to other more rigid bonds, e.g., welds or bonds created through the use of solder). Thus, through the use of spaced apart turns at the wire coil proximal end portion 24 and their being secured to the core 12 at its proximal end (via use of an adhesive as the bonding agent 28), the wire coil 22 is found to be exhibit enhanced flexibility properties, as further described below.

Another feature providing enhanced functioning for the guidewire 10 is the shoulder 30 and the cylindrical portion 34 of the core 12. One purpose of the cylindrical portion 34 is to generally center the wire coil 22 on the distal section 16 of the core 12 about the longitudinal axis of the guidewire 10. By providing the shoulder 30 in combination with the cylindrical portion 34, a space is specifically provided around the core 12 to seat the end of the proximal end portion 24 of the wire coil 22. Through such seating and further securing to the core 12 at its proximal end (via use of the bonding agent 28), the wire coil 22 is found to exhibit good pushability properties across the length of the core's distal section 16 (derived from the core proximal section 14). In certain embodiments, an adhesive is used for the bonding agent 28. Consequently, the junction area between the proximal end portion 24 of the wire coil 22 and the core enables the guidewire 10 to be repeatedly bent at this junction area when being advanced through a patient's body lumens or vessels without excessive stress at the junction area.

As mentioned above, the core 12 can be formed of any metal or combination of metals. In some cases, the core 12 is formed of at least one material that exhibits favorable strength characteristics (i.e., having good stiffness). In certain embodiments, such material involves stainless steel; however, the invention should not be limited to such. As described above, by being at least partially formed of such stiff material, the guidewire 10 can be made to exhibit good pushability properties. Unfortunately, as further described above, guidewires exhibiting good pushability tend to have poor flexibility at their distal sections. However, a decreased profile of the core 12 at its distal section 16 enables the guidewire 10 to exhibit certain lateral flexibility at its distal section. As shown, the wire coil 22, across the majority of its length, is spaced radially outward from the distal section 16 of the core 12, thereby providing an air space there between. As such, the space enables the wire coil 22 to deform when warranted to also contribute to the flexibility in the guidewire's distal section. Further, as described above, spaced apart turns can be provided at the proximal end portion 24 of the wire coil 22 and secured to the core 12 at its proximal end (via use of an adhesive for the bonding agent 28). Consequently, during advancement and/or maneuvering of the guidewire 10, the bond created between the wire coil 22 and the core 12 at this area has flexibility and would be less susceptible to stress-related breakdown.

In other cases, the core 12 can be formed of one or more materials that exhibit favorable flexibility characteristics (i.e., having good bendability). In certain embodiments, such material involves Nitinol; however, the invention should not be limited to such. As described above, by being formed of such flexible material(s), the guidewire 10 tends to have good bending characteristics, yet poor pushability qualities at its distal section. However, by using the shoulder 30 in combination with the cylindrical portion 34 to seat and further secure a certain length of the wire coil's proximal end portion 24 to the core 12 (via the bonding agent 28), the guidewire 10 can be provided to exhibit the pushability at its distal section which is warranted. Furthermore, as described above, in certain embodiments, an adhesive can be used for the bonding agent 28. In turn, the junction area between the proximal end portion 24 of the wire coil 22 and the core exhibits enhanced flexibility as compared to conventional guidewires.

While the proximal end portion 24 of the wire coil 22 can be generally stabilized when being seated via the shoulder 30 and cylindrical portion 34 of the core 12 and further secured via the bonding agent 28, the stability of the rest of the wire coil 22 would often be found to decrease based on the air space between it and the rest of the core's distal section 16. As such, the stiffness modulus of the wire coil 22, and its pushability properties, can be found to decrease distally along the core's distal section 16. However, in certain embodiments, the turns of the wire coil 22 are provided to be small in diameter, e.g., from about 0.001 inch to about 0.003 inch in diameter, so as to provide a minimal transition of stiffness along the length of the tapered distal section 16 of the core 12. As such, the stiffness modulus of the wire coil 22 of the guidewire 10 is found to decrease minimally. Further, because the turns of the wire coil 22 contact each other over a significant portion of the distal section 16 of the core 12, the transition of stiffness along the wire coil 22 is further minimized. As a result, sufficient pushability properties for the guidewire 10 can be effectively maintained over the length of the wire coil 22.

As described above, the bonding agent 28 is used in adhering the proximal end portion 24 of the wire coil 22 to the core 12. In certain embodiments, the bonding agent 28 is applied once the wire coil 22 is positioned on the core 12. Subsequently, the bonding agent 28 is applied to the core 12 for a certain distance 38. In certain embodiments, the distance 38 runs from the shoulder 30, extends along the cylindrical portion 34, and along a further portion of the distal section 16 of the core 12. In applying the bonding agent 28 along the distance 38, the bonding agent 28 fills in the corresponding space between the core 12 and the proximal end portion 24 of the wire coil 22. As should be appreciated, the distance 38 is at least a length sufficient to accommodate enough coil turns so as to properly engage the wire coil 22 with the core 12. In certain embodiments, the number of coil turns needing to be accommodated is at least two turns of the wire coil 22.

As described above, in certain embodiments where the turns of the wire coil 22 are spaced apart at its proximal end portion 24, the bonding agent 28 fills in between some of the coil turns. In such cases, there is an increased surface area for the bonding agent 28 to contact in using spaced coil turns as opposed to using contacting coil turns. As a result, a more significant bond between the core 12 and the wire coil 22 is achieved as opposed to using a wire coil having coil turns in contact with each other throughout its length. In addition, in cases where the bonding agent 28 is flexible, the bonding agent 28 can accordingly flex as the guidewire 12, and in particular, the tapered distal section 16 of the core 12, is advanced and maneuvered through a patient's body lumens or vessels. As a result, the bonding agent 28 is more flexible along the distance 38, and in turn, less inclined to permit the wire coil 22 and/or core to kink or bind at this point/segment of connection. In addition, the bonding agent 28 is more forgiving and more resistive to deterioration and potential breakage due to stress resulting from repetitive bending as opposed to a weld used to secure the proximal end of the wire coil to the core.

As should be appreciated, a drawback to using a wire coil having spaces between consecutive turns is that the wire coil often is limited in its structural strength, particularly across the region when the coil turns are spaced apart. In turn, when such a wire coil is used as described above (i.e., positioned over a tapered distal segment of the guidewire core), there can be a discontinuity in this region with respect to pushability properties. However, such discontinuity can be minimized. For example, in certain embodiments, as shown in FIG. 2A, at least a majority of the spaced coil turns of the wire coil's proximal section 16 are secured to the core 12 via the bonding agent 28. As a result, the bonding agent 28 can be used to provide multiple benefits, including (i) providing an enhanced bond between the core 12 and wire coil 22 and (ii) maintaining the structural strength of the wire coil 22 (so that pushability properties of the guidewire 10 are not compromised). Further, if selectively chosen to be flexible, the bonding agent 28 provides flexibility at the area of enjoinment between the core 12 and the wire coil 22.

Figure 3:
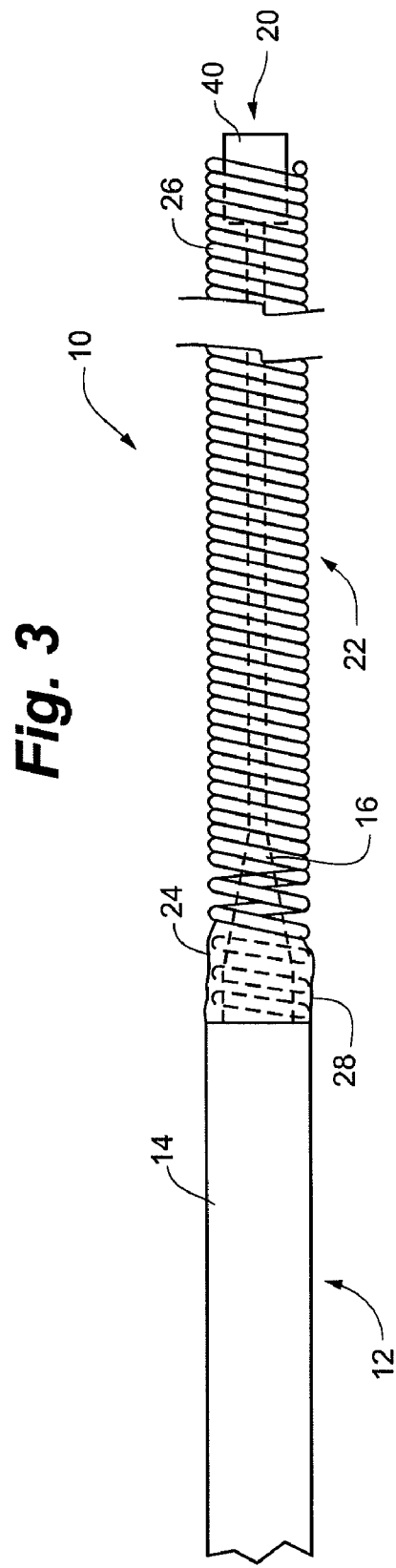
FIG. 3 is a side view of a distal end of the guidewire of FIG. 1 prior to forming.

As alluded to above, in certain embodiments, during manufacture of the guidewire 10, the distal end 20 of the core 12 is generally modified in shape to the expanded portion 18 shown in FIGS. 1, 2 and 2A. As illustrated in FIG. 3, the distal end 20, prior to its modification, can be a compact portion 40 (mostly covered in FIG. 3, but shown with dashed lines where covered). In certain embodiments, the compact portion 40 can be provided so as to have a smaller outer diameter than an inner diameter of the wire coil 22. As a result, prior to being modified in shape, the compact portion 40 would not prevent the wire coil 22 from being slid over the core's tapered distal section 16 during initial assembly of the guidewire 10. As shown, in certain embodiments, once the wire coil 22 is properly positioned over the tapered distal section 16 of the core 12 (so that the proximal end 24 of the wire coil 22 is seated via the shoulder 30 and cylindrical portion 38 of the core 12), the compact portion 40 will at least partially lie within the distal end portion 26 of the wire coil 22. As shown, in certain embodiments, the compact portion 40 of the core distal end 20 resembles a rectangular block; however, as described above, the compact portion 40 can be alternatively provided in any desirable shape.

Following positioning of the wire coil 22 on the tapered distal section 16 of the core, the compact portion 40 of the core distal end 20 is subjected to a process that facilitates the above-described transformation. In certain embodiments, a plasma welding procedure is used, resulting in at least the compact portion 40 being melted so as to change its shape. As should be appreciated, during such process, the compact portion 40 can accordingly be modified to the expanded portion 18. In certain embodiments, following the process, the expanded portion 18 contacts one or more of the distal turns of the wire coil distal end portion 26. As a result, following the process, a secure connection is formed between the expanded portion 18 and the distal end portion 26 of the wire coil 22. As should be appreciated, if the wire coil 22 is made of substantially the same material as the core 12, then the above plasma welding technique will also melt the turns of the wire coil distal end portion 26 located proximate to the distal end 20 of the core 12. If, on the other hand, the wire coil 22 is made of a high-melting material (e.g., tungsten) which does not readily melt from welding, then the distal end 20 of the core 12 will simply melt around the non-melted turns of the wire coil distal end portion 26. In certain embodiments, the distal end 20 is further shaped to form a ball-shaped end (as exemplarily shown in FIGS. 1, 2 and 2A). In turn, the distal end 20 can be provided with a rounded outer surface, which aids in the advancement and maneuvering of the guidewire 10.

Figure 4:
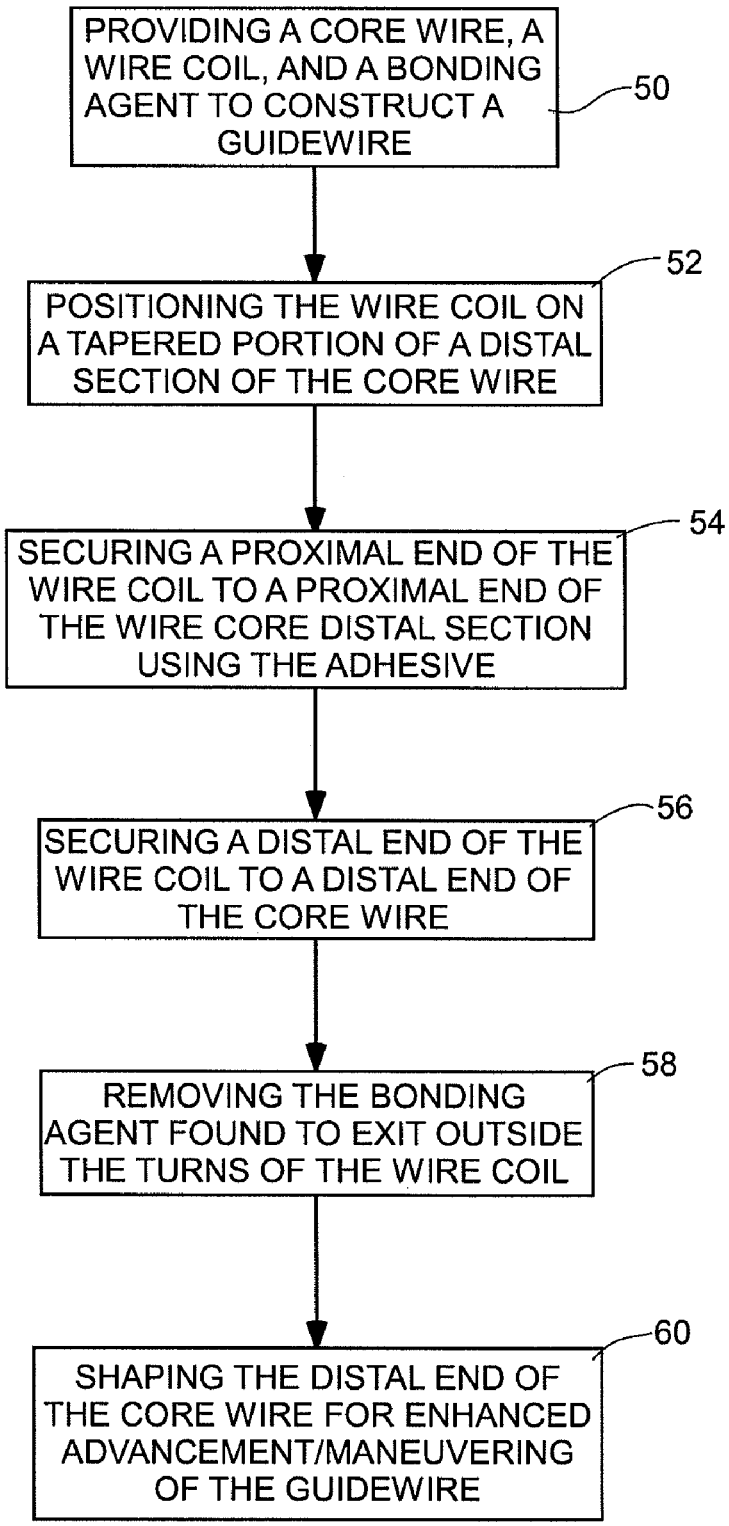
FIG. 4 is a flowchart depicting steps of a method for fabricating the guidewire of FIG. 1.

FIG. 4 provides a method for constructing the guidewire 10 of FIG. 1 in accordance with certain embodiments of the invention. With reference to FIGS. 1-3, an initial step 50 of the method of FIG. 4 involves providing three main elements for constructing the guidewire 10: (i) the metal core 12, (ii) the wire coil 22, and (iii) the bonding agent 28.

As described above, in certain embodiments, the proximal section 14 of the core 12 has a generally uniform diameter, while the distal section 16 has a generally varying diameter with a compact portion 40 at its distal end 20. In certain embodiments, the core 12 has a generally squared-off indentation or shoulder 30 at its proximal end. Further, in certain embodiments, the shoulder 30 extends distally for a certain distance, forming a cylindrical portion 34 of the core 12 immediately distal of the core proximal section 14. As also described above, the wire coil 22 is of sufficient length so as to cover a majority of the core distal section 16. In certain embodiments, the wire coil 22 has a generally uniform outer diameter over its length, which is substantially similar to the diameter of the core proximal section 14. In certain embodiments, the wire coil 22 includes a proximal end portion 24 having coil turns that are spaced apart from one another, and a distal end section 26 having coil turns contacting each other.

Step 52 involves positioning the wire coil 22 on the core distal section 16. As such, the wire coil 22 is received by the core distal section 16. In certain embodiments where the core 12 includes the generally squared-off shoulder 30 and core cylindrical portion 34, the proximal end portion 24 of the wire coil 22 is seated proximate to the shoulder 30 and, in turn, the wire coil 22 is centered by the portion 34. In certain embodiments, once the wire coil 22 is positioned, the distal end 20 of the core 12 will at least partially lie within the wire coil distal end portion 26. Step 54 involves securing the proximal end portion 24 of the wire coil 22 to the proximal end of the core distal section 16. This step involves use of the bonding agent 28. In certain embodiments, the bonding agent 28 is an adhesive. In certain embodiments, the bonding agent 28 is an organic adhesive. In certain embodiments where the core 12 includes the generally squared-off shoulder 30 and core cylindrical portion 34, the bonding agent 28 is applied at the shoulder 30, along the portion 34, and along a further portion of the core distal section 16. Furthermore, in certain embodiments where the wire coil proximal end portion 24 includes coil turns that are spaced apart from one another, the bonding agent 28 fills in between a majority of the spaced apart turns. Following curing, the bonding agent 28 is found to effectively secure the proximal end of the core distal section 16 to the wire coil proximal end portion 24.

Step 56 involves securing the distal end portion 26 of the wire coil 22 to the distal end 20 of the core 12. In certain embodiments, this step involves using a welding process; however, the invention should not be limited to such. Following such process, the compact portion 40 is modified to the expanded portion 18, forming a secure connection between the expanded portion 40 and the distal end portion 26 of the wire coil 22, as already described above.

As should be appreciated, following step 54, there may be some bonding agent 28 that has found to seep around or through the turns of the wire coil proximal end portion 24. As a result, certain of the applied bonding agent 28 will be found to exist outside the coil turns. As described above, in certain embodiments, the wire coil 22 can be provided with substantially the same outer diameter as the diameter of the core proximal section 14 to generally form the guidewire 10 with a generally uniform outer diameter across its length. In turn, there will be limited potential for the guidewire 10 to catch on the patient's body lumens or vessels from significant deviations in the guidewire's outer diameter. Accordingly, step 56 involves removing the applied bonding agent 28 found to exist outside the turns of the wire coil 22 so as to further keep the guidewire's outer diameter generally uniform. As should be appreciated, removing such bonding agent 28 can be provided in a number of manners well known to one skilled in the art.

Step 60 involves shaping the expanded portion 18 to aid in the advancement and maneuvering of the guidewire 10. In certain embodiments, this can involve shaping the expanded portion 18 to have a generally round outer surface. As should be appreciated, shaping of the expanded portion 18 can be provided in a number of manners well known to one skilled in the art.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A medical guidewire, comprising:
   a core having a proximal end and a distal end;
   a wire coil, the core extending through the wire coil, the wire coil in contact with a distal end of the core and extending proximally from the core distal end along an extent of the core, the wire coil having a proximal end portion with spaced apart coil turns with gaps formed between the coil turns, wherein the core has a distally facing shoulder provided uniformly around the core, wherein the shoulder extends axially into the core by a first distance and forms a platform or seat for the wire coil proximal end portion, and wherein the wire coil proximal end portion is seated proximate to the distally facing shoulder; and a bonding agent joining the core to the proximal end portion of the wire coil, the bonding agent comprising an adhesive, the bonding agent filling the gaps between a plurality of the spaced apart coil turns at the proximal end portion of the wire coil, whereby the bonding agent filled in the gaps provides a significant junction area between the core and the wire coil as well as flexibility at the junction area during advancement of the guidewire through a patient's body lumens or vessels, the bonding agent entirely filling area between the plurality of spaced apart coil turns at the proximal end portion of the wire coil and the core.

2. The medical guidewire of claim 1, wherein the first distance is substantially similar in length to a diameter of a coil turn of the wire coil.

3. The medical guidewire of claim 1, wherein the proximal end portion of the wire coil is seated at least proximate to the distally facing shoulder, the distally facing shoulder forming a platform for the wire coil proximal end portion.

4. The medical guidewire of claim 1, wherein the core includes a proximal section and a distal section, wherein the proximal section has a generally uniform diameter and the distal section has a generally varying diameter, and wherein the distally facing shoulder links the proximal section to the distal section.

5. The medical guidewire of claim 4, wherein the wire coil has a generally uniform outer diameter, the wire coil outer diameter being substantially similar to the generally uniform diameter of the core proximal section.

6. The medical guidewire of claim 4, wherein the distally facing shoulder is generally squared off from the generally uniform diameter of the proximal section of the core.

7. The medical guidewire of claim 4, wherein the core distal section includes a cylindrical portion extending distally from the shoulder and a tapered portion extending distally from the cylindrical portion, the cylindrical portion having a generally uniform diameter.

8. The medical guidewire of claim 7, wherein the core distal section further includes an expanded portion distal to the tapered portion, the expanded portion of the core distal section having a diameter substantially similar to the generally uniform diameter of the core proximal section.

9. The medical guidewire of claim 7, wherein the proximal end portion of the wire coil is secured to the core via the bonding agent along a second distance extending from the shoulder along the cylindrical portion and further along a segment of the tapered portion.

10. The medical guidewire of claim 9, wherein the second distance is at least a length sufficient to accommodate a quantity of the spaced apart coil turns warranted to properly secure the proximal end portion of the wire coil to the core.

11. The medical guidewire of claim 10, wherein the warranted quantity of spaced apart coil turns to properly secure the proximal end portion of the wire coil to the core is at least two spaced coil turns of the wire coil.

12. The medical guidewire of claim 1, wherein the spaced apart coil turns at the proximal end of the wire coil have an increased surface area for securement to the bonding agent as opposed to coil turns that are in contact, whereby the spaced apart coil turns with the bonding agent filled in the gaps provides the significant junction area.

13. The medical guidewire of claim 1, wherein the wire coil is generally flexible such that the gaps between the spaced apart coil turns narrow given sufficient force from the advancement of the guidewire.

14. The medical guidewire of claim 13, wherein the bonding agent located in the gaps enables stress resulting from the advancement of the guidewire to be partially absorbed by the bonding agent at the gaps, whereby the bonding agent located in the gaps minimizes potential of the wire coil proximal end deteriorating or breaking from the core.

15. A medical guidewire, comprising:

a core having a generally squared-off distally facing shoulder provided uniformly around the core;

a wire coil having a proximal end portion, the proximal end portion of the wire coil seated at least proximate to the distally facing shoulder, the distally facing shoulder forming a platform for the wire coil proximal end portion whereby the wire coil extends between such shoulder and a distal end of the core; and a bonding agent joining the core to the proximal end portion of the wire coil at the distally facing shoulder, the bonding agent comprising an adhesive, the proximal end portion of the wire coil being stabilized when seated at least proximate to the distally facing shoulder and joined to the core at the distally facing shoulder, whereby the seating and joining of the proximal end portion of the wire coil provides pushability at a distal section of the core during advancement of the guidewire through a patient's body lumens or vessels as well as flexibility at junction area between the core and the wire coil during advancement of the guidewire through a patient's body lumens or vessels, the bonding agent entirely filling area between spaced apart coil turns at the proximal end portion of the wire coil and the core.

16. The medical guidewire of claim 15, wherein the core is formed of metal, wherein the metal comprises any single metal or combination of metals, and wherein the metal exhibits one or more of strength characteristics and flexibility characteristics.

17. The medical guidewire of claim 15, wherein the distally facing shoulder extends axially into the core by a first distance.

18. The medical guidewire of claim 17, wherein the first distance is substantially similar in length to a diameter of a coil turn of the wire coil.

19. The medical guidewire of claim 15, wherein the core includes a proximal section and a distal section, wherein the proximal section has a generally uniform diameter and the distal section has a generally varying diameter, and wherein the distally facing shoulder links the proximal section to the distal section.

20. The medical guidewire of claim 19, wherein the core distal section includes a cylindrical portion extending distally from the shoulder and a tapered portion extending distally from the cylindrical portion, the cylindrical portion having a generally uniform diameter.

21. The medical guidewire of claim 19, wherein the wire coil has a generally uniform outer diameter, the wire coil outer diameter being substantially similar to the generally uniform diameter of the core proximal section.

22. The medical guidewire of claim 15, wherein the wire coil proximal end portion is secured to the core via the bonding agent along a distance extending distally from the distally facing shoulder.

23. The medical guidewire of claim 22, wherein the wire coil has spaced apart coil turns at the proximal end portion, and wherein the distance is at least a length sufficient to accommodate a quantity of the spaced apart turns warranted to properly secure the proximal end portion of the wire coil to the core.

24. The medical guidewire of claim 23, wherein the warranted quantity of spaced apart coil turns to properly secure the proximal end portion of the wire coil to the core is at least two spaced coil turns of the wire coil.

25. The medical guidewire of claim 23, wherein the bonding agent fills one or more gaps between the spaced apart coil turns at the proximal end portion of the wire coil, whereby the bonding agent filled in the gaps provides a significant junction area between the core and the wire coil as well as flexibility at the junction area during the advancement of the guidewire.

26. The medical guidewire of claim 25, wherein the spaced apart coil turns at the proximal end of the wire coil have an increased surface area for securement to the bonding agent as opposed to coil turns that are in contact, whereby the spaced apart coil turns with the bonding agent filled in the gaps provides the significant junction area.

27. The medical guidewire of claim 15, wherein the wire coil includes a distal end portion, the distal end portion having contacting coil turns along length of the distal end portion, whereby the contacting coil turns minimize transition of stiffness along the distal end portion of the wire coil so as to maintain the pushability along the wire coil distal end portion during the advancement of the guidewire.

28. A medical guidewire, comprising:
a core having a generally squared-off distally facing shoulder provided uniformly around the core;
a wire coil having a proximal end portion, the proximal end portion of the wire coil having spaced apart coil turns with gaps formed between the coil turns, the proximal end portion seated at least proximate to the distally facing shoulder, the distally facing shoulder forming a platform for the proximal end portion, whereby the wire coil extends between such shoulder and a distal end of the core; and
a bonding agent joining the core to the proximal end portion of the wire coil, the bonding agent comprising an adhesive, the bonding agent filling the gaps between a plurality of the spaced apart coil turns at the proximal end portion of the wire coil, whereby the bonding agent filled in the gaps provides a significant junction area between the core and the wire coil as well as flexibility at the junction area during advancement of the guidewire through a patient's body lumens or vessels, the bonding agent entirely filling area between the plurality of spaced apart coil turns at the proximal end portion of the wire coil and the core, the proximal end portion of the wire coil being stabilized when seated at least proximate to the distally facing shoulder and joined to the core at the distally facing shoulder, whereby the seating and joining of the proximal end portion of the wire coil provides pushability at a distal section of the core during the advancement of the guidewire.

29. The medical guidewire of claim 28, wherein the spaced apart coil turns at the proximal end of the wire coil have an increased surface area for securement of the bonding agent as opposed to coil turns that are in contact, whereby the spaced apart coil turns with the bonding agent filled in the gaps provides the significant junction area.

30. The medical guidewire of claim 28, wherein the wire coil includes a distal end portion, the distal end portion having contacting coil turns along length of the distal end portion, whereby the contacting coil turns minimize transition of stiffness along the distal end portion of the wire coil so as to maintain the pushability along the wire coil distal end portion during the advancement of the guidewire.

31. The medical guidewire of claim 1, wherein the core includes a proximal section and a distal section, wherein the wire coil extends continuously between the core proximal section and the core distal section, the wire coil representing a lone coil of the core.

32. The medical guidewire of claim 1, wherein the proximal end portion of the wire coil is joined adjacent to the core.

33. The medical guidewire of claim 15, wherein the core includes a proximal section and a distal section, wherein the wire coil extends continuously between the core proximal section and the core distal section, the wire coil representing a lone coil of the core.

34. The medical guidewire of claim 15, wherein the proximal end portion of the wire coil is joined adjacent to the core.

* * * * *